United States Patent [19]
Muriot

[11] 3,982,539
[45] Sept. 28, 1976

[54] MEDICAL/SURGICAL SUCTION EQUIPMENT

[75] Inventor: Edward E. Muriot, Horsham, Pa.

[73] Assignee: Health Technology Labs, Inc., Horsham, Pa.

[22] Filed: Sept. 17, 1975

[21] Appl. No.: 614,226

Related U.S. Application Data

[63] Continuation of Ser. No. 497,838, Aug. 16, 1974, abandoned.

[52] U.S. Cl. .............................................. 128/276
[51] Int. Cl.² ........................................... A61M 1/00
[58] Field of Search .......................... 128/276–278, 128/297–300, DIG. 12, DIG. 24, 214 D, 214 F; 277/178; 220/9, DIG. 9; 312/296; 285/192; 141/59; 27/24 R; 15/314, 353

[56] References Cited
UNITED STATES PATENTS

| | | | |
|---|---|---|---|
| 2,757,669 | 8/1956 | Gewecke et al. | 128/DIG. 12 |
| 3,023,447 | 3/1962 | Senne | 15/314 |
| 3,032,037 | 5/1962 | Huber | 128/276 |
| 3,142,298 | 7/1964 | Koski et al. | 128/276 |
| 3,543,325 | 12/1970 | Hamrick | 15/314 |
| 3,568,239 | 3/1971 | Hamrick | 15/314 |
| 3,640,276 | 2/1972 | Dancy et al. | 128/214 F |
| 3,722,557 | 3/1973 | Huggins | 128/214 D |

Primary Examiner—Robert W. Michell
Assistant Examiner—Henry S. Layton
Attorney, Agent, or Firm—Synnestvedt & Lechner

[57] ABSTRACT

Equipment for medical or surgical uses is provided for purposes, for example, of withdrawing or draining body liquids from cavities tending to accumulate such liquids, for instance as a result of wounds, surgical procedures or of pathological conditions in the body. The equipment comprises a vacuum chamber adapted to receive a disposable collection bag, having a suction line with a catheter for receiving the body liquids, together with control systems for regulating the vacuum in the vacuum chamber and thus the suction in the collection bag.

17 Claims, 10 Drawing Figures

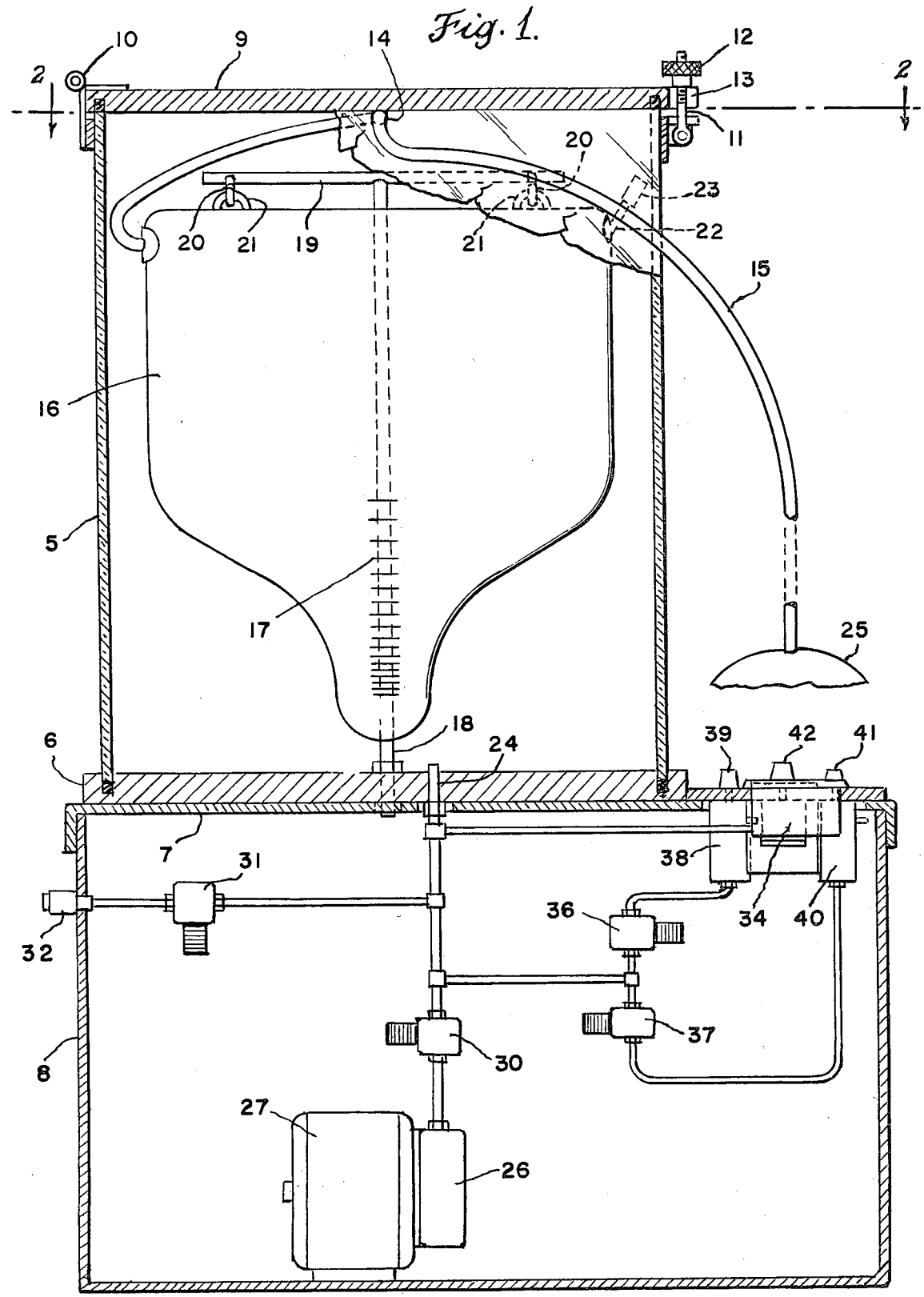

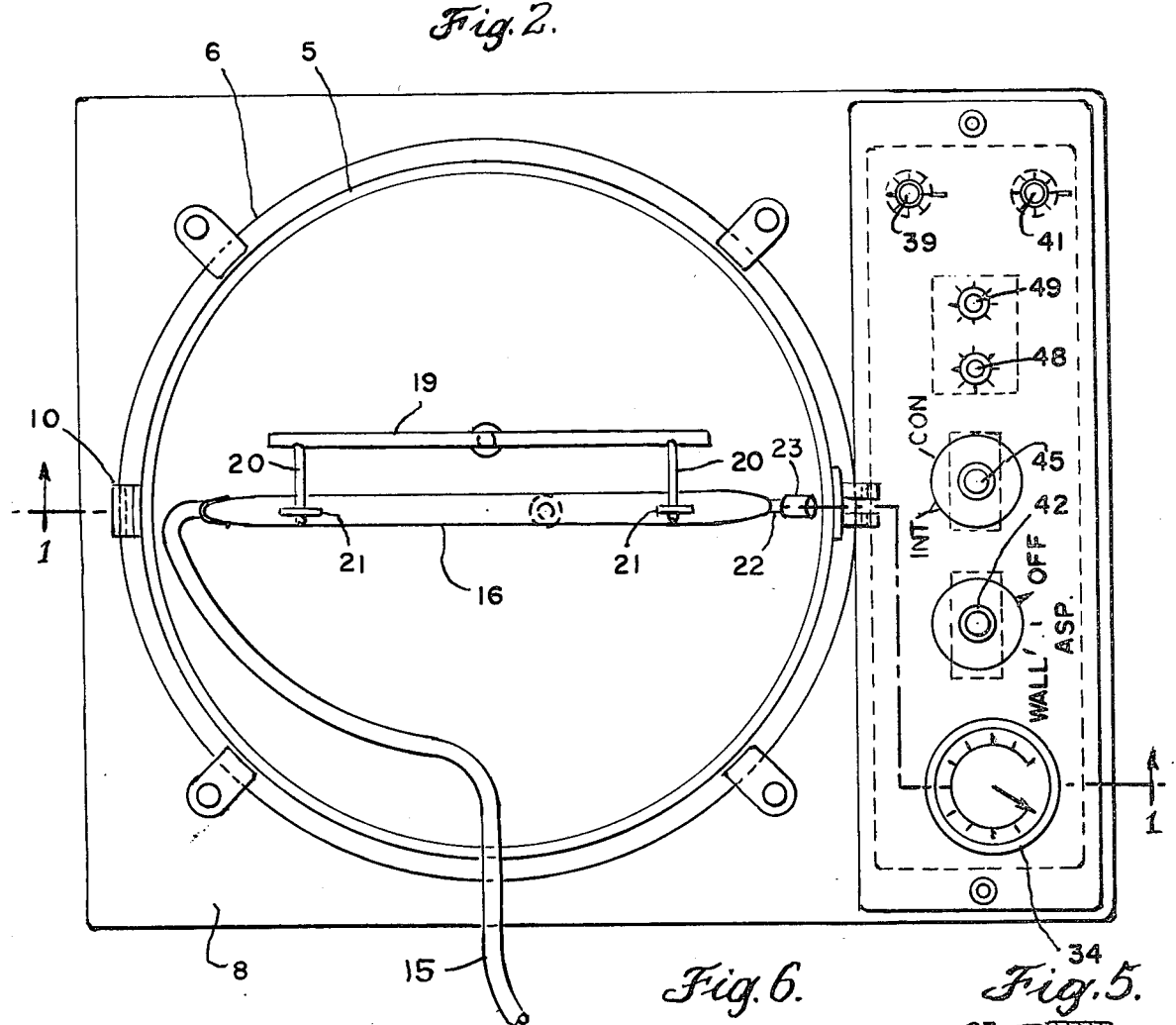
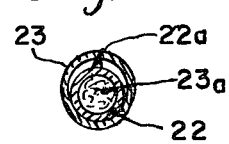
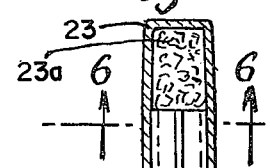
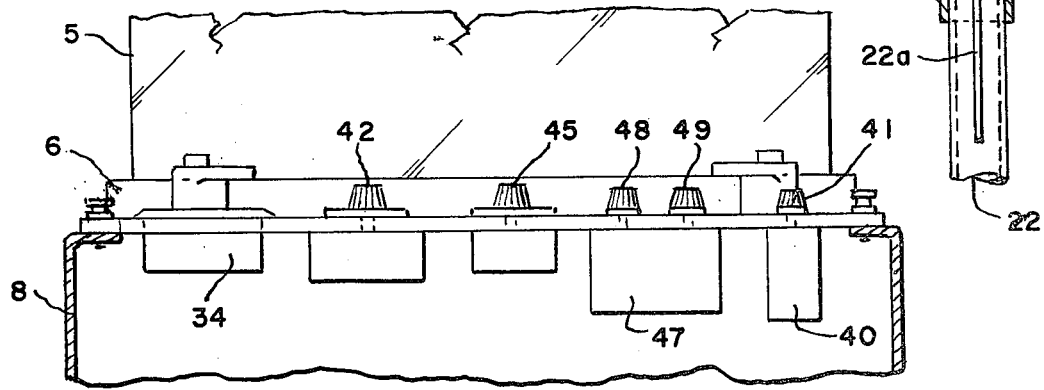

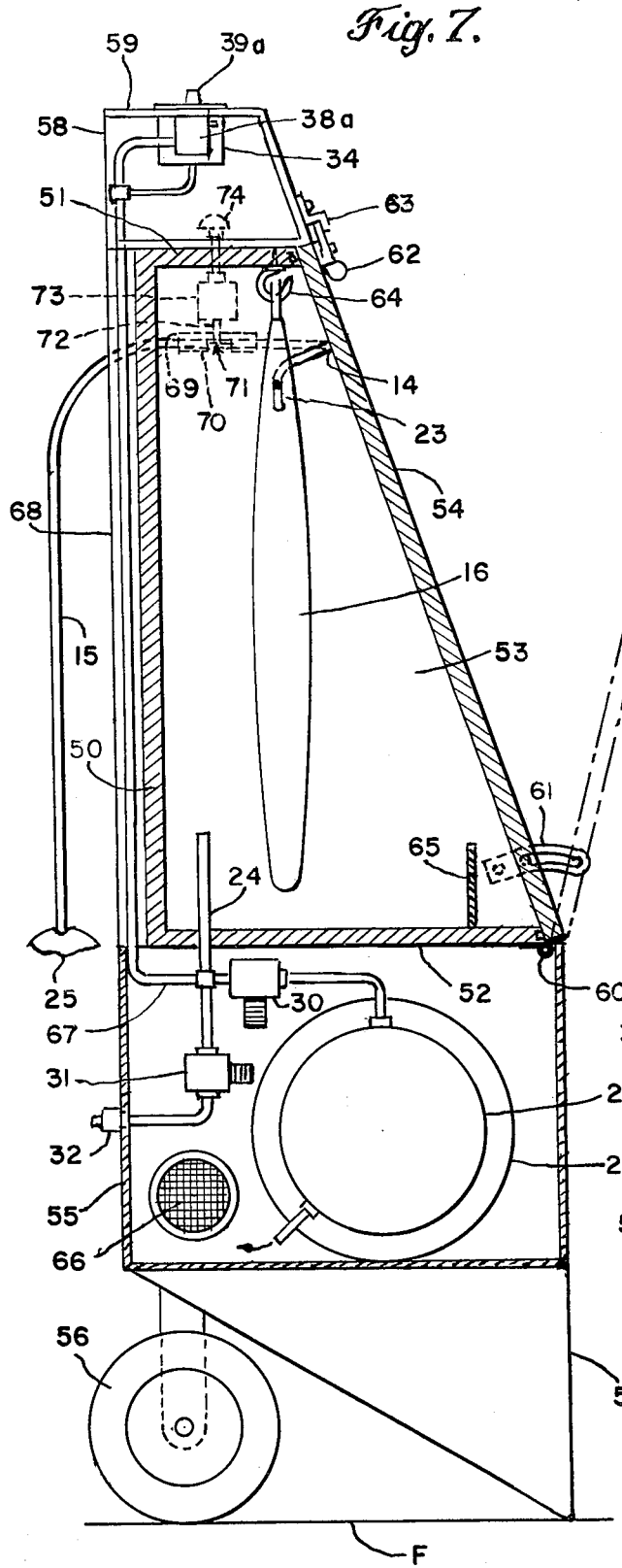
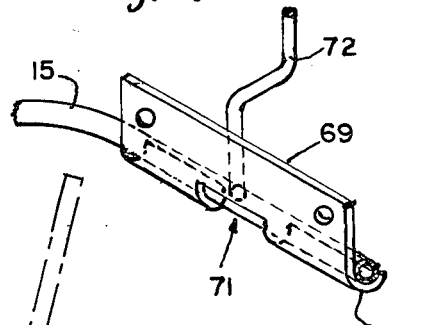
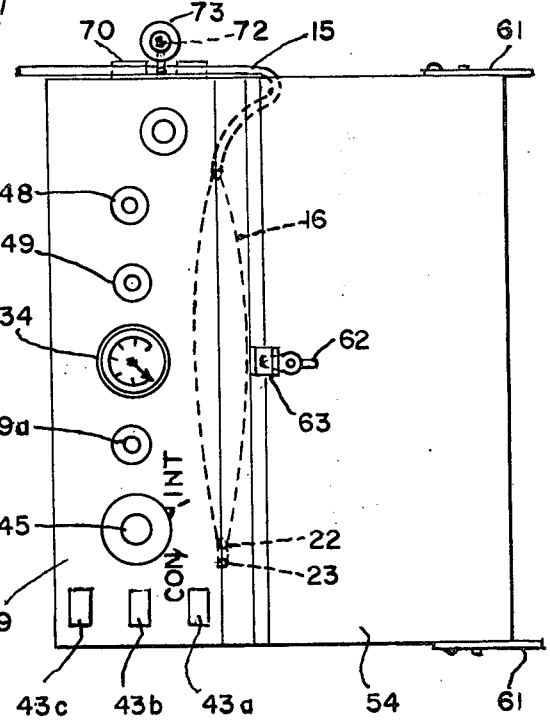

MEDICAL/SURGICAL SUCTION EQUIPMENT

This is a continuation of application Ser No. 497,838, filed Aug. 16, 1974, now abandoned. Certain subject matter of said application 497,838 is also disclosed in companion application Ser. No. 524,052, filed Nov. 15, 1974, and issued June 15, 1976 as U.S. Pat. No. 3,963,027.

The present invention relates to suction equipment for use for medical or surgical purposes, and particularly for the purpose of withdrawing from the body liquids tending to accumulate in cavities or regions of the body because of disease or malfunction or other pathological conditions, or because of surgical or medical procedures. Such conditions at times may also tend to accumulate solids, and it will be understood that the equipment of the invention may also serve to withdraw such solids in suspension in liquids being withdrawn.

One of the principal objectives of the present invention is to provide equipment of the type referred to which is arranged to function on the vacuum or suction principle, without the flow of the liquids through a mechanical pump or pumping mechanism, as has been the case in certain prior arrangements.

A further object of the invention is to provide a high degree of flexibility in the control of the suction, both with respect to the amount of suction applied, and also with respect to the timing thereof. Thus, according to the invention, provision is made not only for adjustment for the amount of vacuum or suction, but also for alternative conditions of operation in which the suction may either be applied continuously or may be applied intermittently.

Still further, it is an object of the invention to provide for operation of the equipment intermittently, with provision for regulation of the duration of the suction intervals as well as for the duration of the "pauses" between the periods when suction is applied.

In accordance with another aspect of the invention, the equipment includes a vacuum chamber adapted to receive an expandable and disposable suction bag having a catheter extended therefrom through the wall of the vacuum chamber so that it may be placed in the wound or other cavity from which drainage is desired.

It is an object of the invention to provide an exceedingly simple and effective system for replacing the disposable bag and catheter, notwithstanding the normal enclosure thereof in the vacuum chamber.

In one embodiment of the invention intermittent operation is achieved by alternately interrupting and reestablishing the vacuum in the vacuum chamber. In a second embodiment intermittent operation is achieved by alternately closing and opening the suction line extended from the collection bag to the intake catheter. In the second embodiment it is an objective to provide for intermittent operation without changing the pressure in the vacuum chamber and also without risk of any backflow in the suction line extended from the suction bag to the intake catheter.

How the foregoing and other objects and advantages are attained will appear more fully from the following description referring to the accompanying drawings, in which:

FIG. 1 is an elevational view, mostly in vertical section, of the physical arrangment of the major components of a first embodiment of equipment constructed according to the present invention, taken as indicated by the line 1—1 on FIG. 2;

FIG. 2 is a plan view, with the top cover of the vacuum chamber removed, taken as indicated by the line 2—2 on FIG. 1;

FIG. 3 is a fragmentary view taken from the right of FIG. 2 and illustrating the location and arrangement of the controls and certain other parts;

FIG. 5 is a fragmentary axial sectional view of the outlet tube of the bag;

FIG. 6 is a crossectional view taken as indicated by the section lines 6—6 in FIG. 5.

FIG. 7 is a vertical sectional view of an alternative embodiment of the suction equipment of the present invention;

FIG. 8 is a plan view of the equipment shown in FIG. 7;

FIG. 9 is an enlarged isometric fragmentary view of a device used for establishing intermittent operation in the embodiment of FIGS. 7 and 8.

Figure 4:
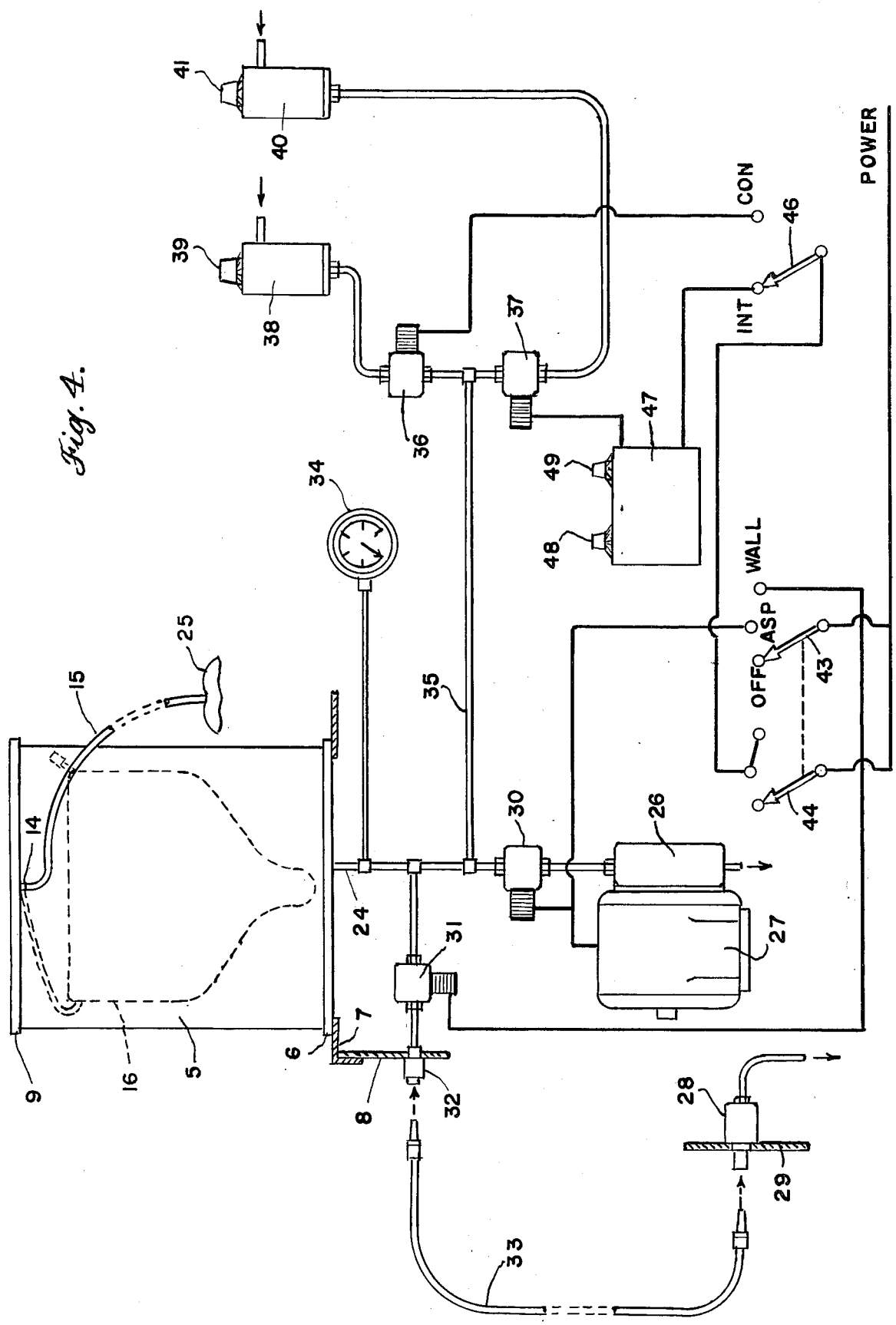
FIG. 4 is a schematic view of the fluid pressure controls and control system for the equipment of the first embodiment, and also certain electrical controls associated therewith.

Referring first to the first embodiment as shown in FIGS. 1, 2 and 3, a vacuum chamber is provided, being formed by a cylindrical body 5, preferably made of transparent material, such as polymethyl methacrylate, but it is to be understood the main body of the chamber may be constructed in various different ways. The cylindrical body 5 has its lower edge sealed in a groove provided in the base plate 6, which is mounted on the top deck 7 of a base or cabinet 8 in which some of the controls and other equipment are housed. These major components of the system are preferably arranged as a portable unit which may be taken to any desired point of use.

At the top of the cylindrical body 5 there is a removable or separable closure plate 9, which is also desirably formed of transparent plastic material and which is hinged to the cylindrical body 5 as indicated at 10 and which further has a separable fastener such as the swing bolt 11 provided with a knurled nut 12, the bolt 11 being accommodated in a recess 13 formed in the edge of the lid 9.

The upper edge of the cylindrical body 5 is also provided with a notch or recess 14 to accommodate the suction tube 15 which is connected with the suction bag 16 arranged within the vacuum chamber. Suction bag 16 with the tube 15 desirably constitutes a disposable unit. These parts are desirably formed of flexible plastic material, preferably transparent or at least translucent so that the quantity of liquid in the bag may be observed and the bag may have a series of graduations 17 from which a reading may be taken of the volume of liquids contained in the bag.

The various parts of the vacuum chamber are sealed to each other in order to prevent loss of vacuum, and the notch 14 for the tube 15 should fit snugly, preferably with a sealing element therebetween.

The bag has a suction tube 15 which may terminate in or be provided with a disposable catheter for insertion into the zone or cavity from which the liquids are to be withdrawn. The bag also has a drain spout 22 with a cap 23 connected with the bag in an upper portion thereof above the normal level to which the bag is filled. The details of construction of the spout and cap appear in FIGS. 5 and 6. Tube 22 has a longitudinal rib 22a, so that when the cap 23 is applied there remain small leakage passages at each side of the rib 22a. This provides for communication of the vacuum in the chamber into the interior of the bag, so that the actual transfer of the liquids is effected under the influence of atmospheric or other pressure upon the liquids in the region of the catheter, which pressure, and the reduced pressure established in the bag by the vacuum provides the pressure differential which is effective to transfer the liquids from the zone being drained into the bag. A wad of cotton or other similar material 23a in the cap 23 acts as a filter preventing transfer of liquid or contaminants from the bag into the surrounding vacuum chamber. If desired the cap may be removed to permit use of the spout 22 as a drainage tube for emptying the bag, for purposes of analysis, test or disposal.

The bag may be supported within the vacuum chamber by various supporting devices preferably cooperating with the top portion of the bag, as by a standard 18 having a cross bar 19 at the top with a pair of hooks 20 adapted to be received in the loops 21 provided at the top edge of the bag. With the bag suspended at the top as just described and with the closure 9 displaceable upwardly about the hinge 10 and still further with the notch 14 in the upper edge of the cylindrical body 5 for receiving the tube 15, the insertion and replacement of the disposable bags is exceedingly simple and may be effected with minimum effort and time.

The suspension of the bag at the top, as shown, and the connection of the suction tube 15 with the upper region of the bag is also advantageous because this arrangement avoids interference with or alteration of the suction as a result of built up of the body of liquid within the bag. If the suction tube 15 were connected with the bottom or in the bottom region of the bag, the gravity head of the accumulating liquid would interfere with and reduce the suction action, and this is avoided by arranging the suction connection so that it communicates with the suction bag in the upper portion thereof, and in any event above the level to which it is intended that the liquid would be permitted to rise in the bag.

As above mentioned, the base or cabinet 8 houses various parts of the controls and control system and the pressure reduction within the vacuum chamber 5 is effected through a vacuum connection 24, preferably arranged in the bottom of the chamber and extended therefrom downwardly for association with the control system housed within the base 8. The various parts of the control system are hereinafter described first with reference to FIG. 4 where the control system is illustrated schematically. In FIG. 4 the vacuum chamber and the suction bag are also indicated somewhat diagrammatically, and in both FIGS. 1 and 4 the suction tube 15 is indicated as having its catheter or free end associated with a portion of a body, diagrammatically indicated at 25, from which it is desired to withdraw liquids.

In the preferred embodiment of the equipment, it is contemplated that the pressure reduction may be effected as a result of association of the vacuum connection 24 with either one of two pressure reduction sources. One of these comprises a self-contained suction or aspirator pump indicated at 26, driven by a motor 27 and housed within the base 8 of the equipment. Alternatively, it is contemplated that the vacuum connection 24 may be coupled with a so-called "vacuum outlet" which is commonly available in hospital rooms as a "plug in" vacuum connection coupling, usually provided on the wall near the head end of the hospital bed. Such a coupling is indicated at 28 in FIG. 4, provided in the wall 29 of the hospital room.

The first of these two sources of vacuum (the pump 26) is coupled with the connection 24 through a normally closed solenoid operated valve 30. The second of these two sources is adapted to be coupled with the vacuum connection 24 through another normally closed solenoid operated valve 31 which, in turn, is connected with a coupler 32 provided in the wall of the base 8. A removable length of tubing 33 having separable couplers at both ends serves to connect the wall outlet 28 with the coupling 32, and thereby provide for completion of the flow path from the vacuum connection 24 to the vacuum wall outlet 28.

A pressure gauge 34 is associated with the connection 24 in order to provide a reading of the pressure level or vacuum established within the vacuum chamber 5.

Tubing 35 is extended from the vacuum connection 24 to a pair of additional normally closed solenoid actuated valves 36 and 37. The valve 36 has associated therewith a bleed valve 38 adjustable by means of a knob 39. Similarly, the valve 37 has associated thereiwth a bleed valve 40 adjustable by means of a knob 41. These two bleed valves are respectively effective when the valves 36 and 37 are opened to provide for regulation of the vacuum, i.e., of the extent of pressure reduction in the chamber 5. It will be understood that in general, the sources of pressure reduction 26 and 28 represent substantially constant pressure reduction sources of relatively high value, so that if the pressure reduction from either of these sources is communicated to the vacuum chamber, without some reduction, for most purposes the vacuum and suction developed would be higher thann that desired. Therefore, one or the other of the adjustable bleed valves 38 or 40 is employed to bleed air at atmospheric pressure into the system and thereby diminish the extent of pressure reduction or vacuum which will be developed in the vacuum chamber 5.

The control by which an operator may select which of the two pressure reduction sources (26 or 28) is to be employed constitutes a switch in an electrical control circuit which is indicated in FIG. 4 purely diagrammatically. This control switch comprises a control knob 42 (see FIGS. 2 and 3) having two ganged switch levers 43 and 44 (see FIG. 4). The switch lever 43 controls the solenoid operated valves 30 and 31, having three positions, namely OFF, ASP, and WALL. In the OFF position both of the valves 30 and 31 remain closed and the vacuum system is out of service. In the ASP position the valve 30 is opened and the motor 27 is operating so that the pressure reduction is derived from the internally located aspirator pump 26. In the WALL position the valve 31 is opened and the pressure reduction is derived from the wall outlet 28.

It will be noted that in either the ASP or WALL position, the ganged second switch lever 44 provides for delivery of power to another switch having a knob 45 (see FIGS. 2 and 3) operating a switch lever 46 which may selectively or alternatively be positioned in the INT or the CON positions, as indicated in FIG. 4. In the CON position the solenoid valve 36 is opened and the bleed valve 38 is effective to regulate the pressure reduction in the chamber 5, and this represents a constant operating condition which may be maintained at any desired pressure level according to the adjustment of the knob 39.

When the switch lever 46 is in the INT position, the valve 37 may be opened, but this opening is effected under the influence of the timer device indicated at 47. The timer has two controls 48 and 49, the first providing for control of the period of time during which the valve 37 is opened, and the second providing for control of the length oof the interval between the periods during which the valve 37 is opened. In this way the suction may be made intermittent, as is sometimes desirable in order to provide for withdrawal of body liquids for only short periods of time, at timed intervals. It will be understood that any suitable switches, solenoids, timers and the like may be utilized, such individual components forming no part of the present invention per se.

From the foregoing it will be seen that the equipment of the first embodiment of the invention provides great flexibility in control and in the operating conditions, the extent of pressure reduction being variable at will by the bleed valves 38 and 40, which are respectively operative either in the continuous mode or in the intermittent mode, and this regardless of which of the pressure sources is relied upon to effect pressure reduction in the vacuum chamber.

Turning now to the embodiment illustrated in FIGS. 7–10 inclusive, it is first pointed out that a number of parts and devices employed are the same or essentially the same as those utilized in the first embodiment and described above. The same reference numerals are employed on such parts or components and they will be referred to in the following description only generally, instead of in detail in view of the description previously given.

The embodiment of FIGS. 7–10 incorporates a number of distinctive features as compared with the first embodiment and these distinctive features are emphasized in the following description.

Reference is first made to the overall general configuration of the equipment shown in FIGS. 7–10 and it will be seen that the vacuum chamber of this embodiment is made up of assembled flat sheets or wall elements, at least some of which are preferably formed of transparent plastic or resin material such as polymethyl methacrylate. The vacuum chamber is defined by a back wall 50, top and bottom walls 51 and 52, upright end walls 53, and an inclined front wall 54. At least the front wall 54, which is arranged to serve as a door or closure, as more fully brought out herebelow, is preferably formed of transparent material, and desirably also the side walls. The vacuum chamber is arranged above a base 55 adapted to enclose certain operating parts, as will further appear, this base desirably being substantially completely enclosed, except for certain ports or passages through which connections extend, as will be described. Below the bottom wall of the base or enclosure 55 means for supporting the unit are provided, preferably including a pair of laterally spaced wheels 56, and a pair of downwardly projecting spaced side wall elements 57, which may conveniently take the form of triangular pieces, with one corner of each presented downwardly to provide for support as on the floor indicated at F in FIG. 7.

With the equipment arranged in the general manner described above, the various components are conveniently arranged and assembled in an overall structure which may readily be wheeled from place to place and which will also stand in a stable upright position because of the supporting elements 56 and 57.

With regard to the general arrangement it is further to be observed that superimposed above the top wall 51 of the vacuum chamber a control box is provided as indicated at 58, this box having a top wall or panel 59 with which various of the operating controls are associated, especially those which are located within the control box 58.

The inclined front wall 54 is preferably hinged along its lower edge as indicated at 60 so that this wall serves as a displaceable closure movable between the full line closed position shown in FIG. 7 at 54 and the dot-dash open position 54a. Straps 61 each having a slot cooperating with a pin are provided to limit the opening movement of the front wall in the manner plainly shown in FIG. 7. The wall 54 may be fastened in closed position by means of a pivoted latch device 62 cooperating with a keeper 63.

Opening the front panel provides for ready access to the suction bag 16, which is conveniently hung from hooks 64 depending from the top wall 51 of the vacuum chamber. The bag is desirably of the construction described above, having a suction tube 15 and also a drain 22 with cap 23 constructed as described. Along the edge of one of the side walls 53, a notch 14 is provided to accommodate the suction tube 15, in a manner very similar to the arangement shown in the first embodiment. It will be understood that sealing gaskets or other sealing elements will be employed to avoid leakage and loss of vacuum, for instance along the meeting edges of the displaceable wall 54 and the side, top and bottom walls of the chamber, as well as in the region of the notch 14 for accommodation of the suction tube 15.

In the bottom portion of the suction chamber an upright wall 65 is provided, projecting upwardly from the bottom wall 52 and extending laterally between the side walls 53, this wall 65, cooperating with other wall elements of the vacuum chamber to define a sump which will receive and retain liquids, in the event of inadvertent spillage or leakage, for instance because of a damaged suction bag. Preferably the wall 65 is of sufficient vertical height so that the sump provided has a volumetric capacity at least as great as the normal charge in one of the suction bags. It will also be noted that the vacuum connection 24 which extends upwardly through the bottom wall of the vacuum chamber extends to a height somewhat above theuupper edge of the wall 65, so that even in the event of accumulation of liquid in the sump, this liquid will not enter the vacuum system.

It is contemplated that the equipment shown in FIGS. 7–10 be capable of operation either by the action of a self-contained aspirator comprising the suction pump 26 and motor 27, or by an externally available vacuum source which may be coupled with the equipment by means of the plug-in vacuum connection 33 of the kind above described, cooperating with the connector 32. These two sources of vacuum are respectively controlled by normally closed solenoid operated valves 30 and 31 as in the first embodiment, both of these valves being associated with the vacuum connection 24 which is extended from the base enclosure upwardly into the vacuum chamber. Preferably the base enclosure 55 is provided with an opening with which a filter device 66 is associated, desirablly in the form of a replaceable filter unit, so that any discharge through the opening from the interior of the base enclosure from the suction pump 26 will be filtered before discharge into the surrounding air.

Figure 10:
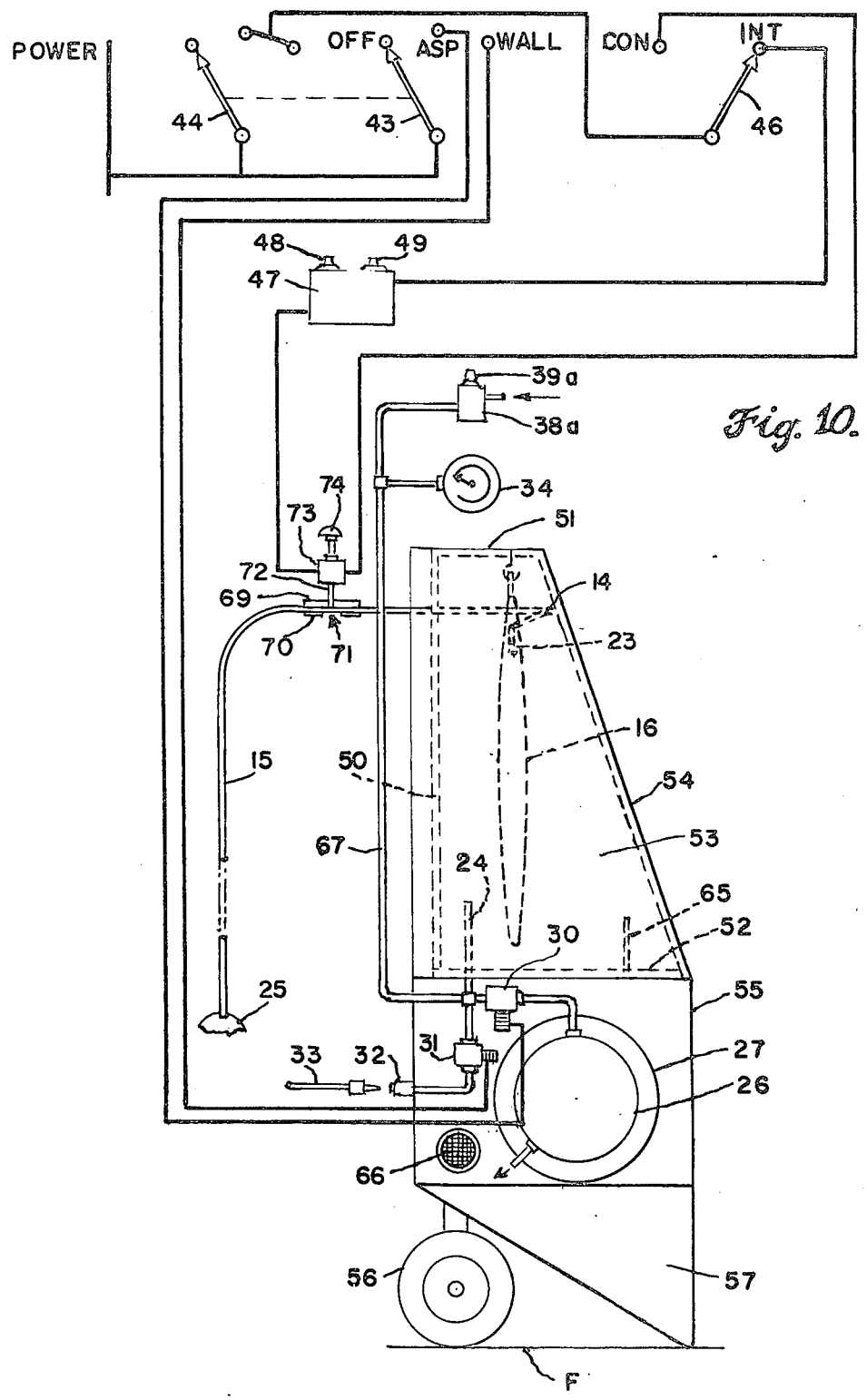
FIG. 10 is a schematic view of the fluid pressure and other controls employed with the equipment of FIGS. 7, 8 and 9.

The arrangement of the controls appears to best advantage in the schematic view of FIG. 10. Here it will be seen that the vacuum connection 24 which communicates with the intake sides of the solenoid valves 30 and 31, also communicates with a connection 67 which extends from the base enclosure upwardly at the back of the vacuum chamber, for instance through an enclosed duct or channel 68 (see especially FIG. 7), this connection 67 being associated with controls arranged in the control box 58 at the top of the unit, as described below with particular reference to the schematic view of FIG. 10.

A pressure gauge 34 is associated with the vacuum line 67, and in addition an adjustable bleed valve 38a, having an adjustable control knob 39a is associated with the vacuum connection 67, these devices (34 and 39a) being mounted on the panel 59 at the top of the control box, as will be seen from FIG. 8. The timer device 47 is also located in this control box and the two control knobs 48 and 49 of this timer are positioned above the panel 59 as also appears in FIG. 8.

The timer mechanism in the embodiment of FIG. 7 is arranged to operate in a somewhat different manner than in the embodiment of FIGS. 1–6. Thus, whereas in FIGS. 1–6 the timer mechansim operates on the suction side of the system, i.e., operates on the vacuum connection 24 by means of which the vacuum is developed in the vacuum chamber, in the embodiment of FIGS. 7–10 the timer mechanism is arranged to operate on the suction tube 15 which, in effect, is the pressure side of the system, i.e., the side at which atmospheric pressure is acting to cause flow of the liquids through the tube 15 into the suction bag. Outside of the vacuum chamber, at one side wall thereof, a bracket 69 is provided, the lower edge of this bracket having an upwardly open channel 70 adapted to receive the tube 15. When a bag is inserted in the vacuum chamber and the tube introduced into the notch 14, the tube may also be manually laid into the channel 70 and then extended to the source 25 of the liquid to be drawn into the suction bag. The midportion of the channel 70 is cut away as indicated at 71 in FIG. 9, in a position below the plunger 72 of the solenoid device 73. The solenoid device is of the type in which the plunger 72 is biased downwardly, as by spring pressure, and when the plunger is pressed downwardly against a tube 15 in the channel 70, the tube will be closed by being deflected into the recess 71. The plunger 72 may be manually lifted by the handle 74 provided at the top of the solenoid device. The plunger 72 may also be raised by action of the solenoid under the influence of the timer 47, in which event the raising of the plunger will be intermittent, the control knobs 48 and 49 providing for control of the period during which the plunger is raised and also for control of the interval between periods when the plunger is raised.

The solenoid 73 may be activated constantly, thus maintaining the plunger 72 in raised position at anytime the switch 46 is positioned in the CON position.

As in the first embodiment, the arrangement of FIGS. 7–10 includes a control knob 45 for the switch providing for alternative intermittent or constant operation (see FIG. 8). In addition switch buttons 43a, 43b and 43c are provided on the control panel as shown in FIG. 8, these buttons serving to operate the switch parts indicated at 43 and 44 in FIG. 10 and serving respectively to establish the OFF, ASP and WALL conditions.

The arrangement of the solenoid 73 as described hereinabove, has a number of distinctive advantages including the fact that at anytime when the system is completely turned off, as by pushing the OFF button, the plunger 72 will close the tube 15, which is desirable in order to prevent gravity flow of liquid in reverse direction through the tube 15 to the body cavity from which liquids have been withdrawn.

When the equipment is being operated with the switch 46 in the CON position the plunger 72 will be lifted so that fluids may be drawn through the tube 15 into the suction bag 16. When the switch 46 is in the INT position the plunger 72 will be intermittently raised and lowered, thereby intermittently opening and closing the suction tube 15. This provides an intermittent suction operation without changing the vacuum or pressure reduction in the vacuum chamber and the suction bag. This provides for intermittent operation without involving any time delays for pressure reduction or pressure increase in the vacuum chamber. The positioning of the tube 15 in the channel 70 is a simple and readily effected operation, merely requiring manual lifting of the spring pressed plunger 72 by the handle 74, in order to raise the plunger to a position above that established by the solenoid and its return spring, so that the tube may readily be placed in the channel 70 below the plunger 72. Upon release of the handle the plunger will descend under the action of the return spring to close the tube, unless the equipment is in operation, in which event the plunger will be kept by the control circuits in the position shown in which the tube is open.

In both embodiments, the use of the vacuum system to produce the suction in the suction bag is advantageous from a number of standpoints including the fact that this system facilitates the employment of disposable suction bag and suction tube components. It will be observed that no part of the disposable components need be introduced into any mechanical pump device. Moreover, the system of the present invention is capable of establishing and maintaining a given suction condition immediately from outset of operation, and this condition will be maintained at the selected suction or pressure level without variation, regardless of fluctuations of the quantity of liquid in the suction tube or in the suction bag.

The equipment is simple, inexpensive and reliable and presents virtually no hazards from the standpoint of contamination of the non-disposable portions of the apparatus.

The embodiment of FIGS. 7–10 is also very flexible and adaptable to use under a variety of conditions and in a variety of positions, since the equipment may readily be wheeled from place to place. The arrangement of the vacuum chamber in the embodiment of FIGS. 7–10, with the pivotally mounted door or closure 54 also provides maximum convenience in introducing and removing the suction bags.

I claim:

1. Equipment for withdrawing body liquids comprising a vacuum chamber, a suction bag removably positioned in the vacuum chamber and having an opening for interconnecting the interior of the bag with the interior of the chamber, the bag further having an inlet connection comprising a tube the wall of which is connected with the wall of the bag and extended therefrom to a point exterior of the vacuum chamber for intake of body liquid, a vacuum line adapted to be connected with a pressure reduction source of substantially constant reduced pressure, said line being connected with the vacuum chamber independently of the bag and being in communication with the interior of the vacuum chamber externally of the bag, and means for varying the pressure reduction in the vacuum chamber and thereby varying the suction in said bag comprising an adjustable bleed valve for introducing air into said line, the bag and tube being unitarily removable from the vacuum chamber independently of said vacuum line.

2. Equipment as defined in claim 1 and further including control mechanism providing for timed intermittent fluctuation of pressure reduction.

3. Equipment as defined in claim 2 in which the control mechanism comprises a shut-off valve in said vacuum line and a timer for periodically opening and closing said shut-off valve.

4. Equipment as defined in claim 3 in which the timer comprises means for regulating the intervals between and the duration of the opening and closing of the shut-off valve.

5. Equipment as defined in claim 2 which the control mechanism comprises a a pinch valve for shutting off the bag inlet tube, and means for opening and closing said pinch valve at timed intervals.

6. Equipment for withdrawing body liquids comprising a vacuum chamber having a removable closure, a suction bag adapted to be inserted into and removed from the vacuum chamber when said closure is removed and having an inlet connection comprising a tube with the tube wall connected with the wall of the bag and unitarily separable from the vacuum chamber and its closure to provide for unitary removal and replacement of the bag and tube, the tube being extended from the bag to a point exterior of the vacuum chamber for intake of body liquid, the bag further having an opening communicating with the interior of the vacuum chamber, a vacuum line adapted to be connected with a pressure reduction source of substantially constant reduced pressure, said line being connected with the vacuum chamber independently of the bag and being in communication with the interior of the vacuum chamber externally of the bag, means for periodically varying the pressure reduction in the vacuum chamber and thereby periodically varying the suction in said bag, and means preventing back flow of liquid in the inlet connection during intervals of diminished pressure reduction in the vacuum chamber.

7. Equipment as defined in claim 6 in which said means for periodically varying the pressure reduction in the vacuum chamber is adjustable to periodically restore the pressure in said chamber to atmospheric pressure.

8. Equipment for withdrawing body liquids comprising a vacuum chamber, a suction bag adapted to be removably positioned in the vacuum chamber and having an opening for interconnecting the interior of the bag with the interior of the chamber, the bag further having an inlet connection comprising a flexible tube with the tube wall connected with the wall of the bag and unitarily removable therewith, the tube being extended from the bag to a point exterior of the vacuum chamber for intake of body liquid, a vacuum line adapted to be connected alternatively with either one of two pressure-reduction sources, said line being connected with the vacuum chamber independently of the bag and being in communication with the interior of the vacuum chamber externally of the bag, and controllable valve means for alternatively connecting said line with either one of said sources.

9. Equipment as defined in claim 8 and further including control means provided alternatively for maintenance of continuous or intermittent pressure reduction in the vacuum chamber.

10. Equipment as defined in claim 8 and further including control mechanism for intermittently closing and opening the inlet connection of the bag.

11. Equipment for withdrawing body liquids comprising a vacuum chamber, a suction bag adapted to be removably positioned in the vacuum chamber and having an inlet connection comprising a tube with the tube all connected with the wall of the bag and unitarily removable from the vacuum chamber, the tube being extended from the bag to a point exterior of the vacuum chamber for intake of body liquid, the bag further having an opening communicating with the interior of the vacuum chamber, a vacuum line adapted to be connected with a pressure reduction source of substantially constant reduced pressure, said line being connected with the vacuum chamber independently of the bag and being in communication with the interior of the vacuum chamber externally of the bag, control means providing alternatively for establishment of conditions of continuous and intermittent pressure reduction in the vacuum chamber, and means preventing back flow of liquid in the inlet connection in the intervals between periods of said intermittent pressure reduction in the vacuum chamber.

12. Equipment for withdrawing body liquids comprising a chamber having an imperforate wall structure and a displaceable closure member cooperating to define a closed but openable vacuum compartment for receiving a disposable suction bag having a liquid inlet tube with the tube wall connected with the wall of the bag, said imperforate wall structure and said closure having poritons cooperating to form a channel through which the bag inlet tube may be extended and providing for unitary separation of the bag and tube from the vacuum chamber and its closure member and thus for unitary removal and insertion of bags with connected inlet tubes, means for suspending a suction bag in said compartment with its inlet tube extended through said channel, and means for effecting pressure reduction in said compartment thereby drawing body liquids into a suction bag suspended in said compartment through the inlet tube for the bag.

13. Equipment for withdrawing body liquids comprising a chamber having an imperforate wall structure and a displaceable closure member cooperating to define a closed but openable vacuum compartment, a replaceable suction bag in said compartment having an opening for interconnecting the interior of the bag with said compartment and further having a liquid inlet tube with the tube wall connected with the wall of the bag, said imperforate wall structure and said closure member having portions cooperating to form a channel through which the bag inlet tube may be extended and providing for unitary separation of the bag and tube from said imperforate wall structure and said closure member and thus for unitary removal and insertion of bags with connected inlet tubes, means for suspending the suction bag in said compartment with its inlet tube extended through said channel, and means for effecting pressure reduction in said compartment thereby drawing body liquids into the suction bag suspended in said compartment through the inlet tube for the bag.

14. Equipment as defined in claim 13 in which the wall of the inlet tube is connected with the wall of the bag in the upper portion of the latter and in which the channel for the inlet tube formed between the displaceable closure and the imperforate wall structure is arranged in an upper portion of the chamber.

15. Equipment for withdrawing body liquids comprising a chamber having an imperforate wall structure and a removable closure member cooperating to define a closed but openable vacuum compartment, a suction bag having a liquid inlet tube the wall of which is connected with the wall of the bag, the bag being positioned in the vacuum compartment and having its inlet tube extended to a point exterior of the chamber for intake of body liquid, the bag further having an opening communicating with the interior of the vacuum chamber, a vacuum line adapted to be connected with a pressure-reduction source, said line being in communication with the vacuum compartment externally of the bag, mechanism including valve means providing alternatively for continuous or intermittent pressure reduction in said compartment, and means preventing back flow of liquid in the inlet connection in the intervals between periods of said intermittent pressure reduction in the vacuum chamber.

16. Equipment as defined in claim 15 and further including a valve means providing for alternative connection of said vacuum line with either one of two separate sources of pressure reduction.

17. Equipment for withdrawing body liquids comprising a portable structure including a chamber having an imperforate wall and a displaceable door cooperating to define a closed but openable vacuum compartment, said portable structure further including a vacuum line connected with said vacuum compartment and including a control valve for said vacuum line unitarily associated with the chamber, a replaceable suction bag in said compartment having an opening for interconnecting the interior of the bag with said compartment and further having a liquid inlet tube with the tube wall connected with the wall of the bag, said imperforate wall and said door having portions cooperating to form a channel through which the bag inlet tube may be extended and providing for unitary separation of the bag and tube from said imperforate wall and said door independently of said vacuum line and its control valve.

* * * * *